United States Patent
Timmer et al.

(10) Patent No.: US 7,912,262 B2
(45) Date of Patent: Mar. 22, 2011

(54) IMAGE PROCESSING SYSTEM AND METHOD FOR REGISTRATION OF TWO-DIMENSIONAL WITH THREE-DIMENSIONAL VOLUME DATA DURING INTERVENTIONAL PROCEDURES

(75) Inventors: Jan Timmer, Eindhoven (NL); Robert Johannes Frederik Homan, Eindhoven (NL); Pieter Maria Mielekamp, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 862 days.

(21) Appl. No.: 11/817,801

(22) PCT Filed: Mar. 9, 2006

(86) PCT No.: PCT/IB2006/050733
§ 371 (c)(1),
(2), (4) Date: Sep. 5, 2007

(87) PCT Pub. No.: WO2006/095324
PCT Pub. Date: Sep. 14, 2006

(65) Prior Publication Data
US 2008/0192996 A1 Aug. 14, 2008

(30) Foreign Application Priority Data
Mar. 10, 2005 (EP) .................................. 05101857

(51) Int. Cl.
*G06K 9/00* (2006.01)
(52) U.S. Cl. ............................ 382/128; 128/922; 378/4
(58) Field of Classification Search ................ 382/10, 382/128, 129, 130, 131, 132; 128/922; 378/4–27
See application file for complete search history.

(56) References Cited

U.S. PATENT DOCUMENTS
5,531,520 A * 7/1996 Grimson et al. .............. 382/131
(Continued)

FOREIGN PATENT DOCUMENTS
EP 0860144 A2 8/1998
(Continued)

OTHER PUBLICATIONS
Zolllei, L et al; "2D-3D_Rigid_Registration". Artificial Intelligence Laboratory, Cambridge, MA 02139, IEEE 2001.
(Continued)

*Primary Examiner* — Anand Bhatnagar

(57) ABSTRACT

Prior to an intervention, a 3D rotational scan is acquired (at block 10) in respect of a body volume and reconstructed. In addition, three-dimensional image data in respect of the body volume is acquired (at block 12) using another modality, such as computerised tomography (CT) or magnetic resonance (MR), reconstructed, and prepared for visualisation. During the actual intervention, live two-dimensional fluoroscopic images are acquired (at block 14), using the imaging system employed to acquire the 3D rotational scan, and processed for visualisation. The 2D image data is registered (at block 16) to the 3D rotational image data acquired and reconstructed in respect of the body volume of interest, and then a 3D-3D registration process is employed (at block 18) to register the 3D image data acquired in respect of the same body volume using, for example, CT or MR imaging systems to the 3D rotational image data, and a display module (20) is used to align the 2D fluoroscopic image and the 3D MR/CT image as a fused or composite image and display the image.

9 Claims, 2 Drawing Sheets

U.S. PATENT DOCUMENTS

| | | | |
|---|---|---|---|
| 5,633,951 A * | 5/1997 | Moshfeghi | 382/154 |
| 5,672,877 A | 9/1997 | Liebig et al. | |
| 5,901,119 A | 5/1999 | Inoue | |
| 5,951,475 A * | 9/1999 | Gueziec et al. | 600/425 |
| 6,480,732 B1 * | 11/2002 | Tanaka et al. | 600/425 |
| 6,611,615 B1 * | 8/2003 | Christensen | 382/130 |
| 6,666,579 B2 | 12/2003 | Jensen | |
| 6,714,810 B2 | 3/2004 | Grzeszczuk et al. | |
| 6,728,424 B1 | 4/2004 | Zhu et al. | |
| 7,627,158 B2 * | 12/2009 | Hay | 382/131 |
| 7,715,604 B2 * | 5/2010 | Sun et al. | 382/128 |
| 2003/0063787 A1 | 4/2003 | Natanzon et al. | |
| 2004/0215071 A1 | 10/2004 | Frank et al. | |
| 2005/0049477 A1 | 3/2005 | Fu et al. | |
| 2005/0089205 A1 * | 4/2005 | Kapur et al. | 382/128 |
| 2008/0107312 A1 * | 5/2008 | Von Berg | 382/128 |

FOREIGN PATENT DOCUMENTS

| | | |
|---|---|---|
| WO | 0157805 A2 | 8/2001 |
| WO | 0187136 A2 | 11/2001 |

OTHER PUBLICATIONS

Gary E. Christensen et al; "Invertibility_and_Transitivity_Analysis", University of Iowa, Jan. 2003.

* cited by examiner

IMAGE PROCESSING SYSTEM AND METHOD FOR REGISTRATION OF TWO-DIMENSIONAL WITH THREE-DIMENSIONAL VOLUME DATA DURING INTERVENTIONAL PROCEDURES

This invention relates generally to an image processing and method for registration of live, two dimensional images, acquired during an interventional procedure, with three-dimensional volume data.

Referring to FIGS. 1 and 2 of the drawings, a typical X-ray system comprises a swing arm (C-arc or G-arc) 1 supported proximal a patient table 2 by a robotic arm 3. Housed within the swing arm 1, there is provided an X-ray tube 4 and an X-ray detector 5, the X-ray detector 5 being arranged and configured to receive X-rays 6 which have passed through a patient 7 and generate an electrical signal representative of the intensity distribution thereof. By moving the swing arm 1, the X-ray tube 4 and detector 5 can be placed at any desired location and orientation relative to the patient 7.

In the treatment of various types of condition and disease, a special medical application is provided by the fluoroscopic observation of the propagation of a catheter in the vascular system of the patient. Thus, during intervention, a catheter or guidewire is required to be advanced under X-ray surveillance (fluoroscopy), and as accurately as possible, through the vessels to an internal part of interest. While this procedure is performed, the vessel structures are made visible on a first monitor for short periods of time, in the form of two-dimensional live images, by introducing short bursts of a radio-opaque contrast agent through the catheter and obtaining X-ray images using, for example, the system described with reference to FIGS. 1 and 2 of the drawings.

For the safety of the patient, it is highly desirable to minimise the exposure to X-rays and also to minimise the amount of contrast agent introduced into the body, and it is therefore known to display, during an intervention, on a second monitor, one or more pre-interventional X-ray images acquired in respect of the area of interest, so as to assist navigation. It is further desirable for the physician to be able to visualise in three dimensions, the two-dimensional fluoroscopic image data acquired during the intervention, as this will enable interventional data to be tracked in real time, whilst significantly reducing the contrast fluid and X-ray exposure load on the patient during the interventional procedure.

U.S. Pat. No. 6,666,579 describes a medical imaging system including an X-ray system such as that described with reference to FIGS. 1 and 2, wherein the swing arm is moved through an acquisition path and a plurality of two-dimensional images of a body volume are acquired at different respective positions along the acquision path. An image processor then constructs three-dimensional volume data based on the acquired two-dimensional images and a three-dimensional image of the body volume is displayed. A position tracking system is provided to track the relative positions of the patient and swing arm during the image acquisition, and also to track movement of a surgical instrument through the body volume during an intervention. Two-dimensional images acquired during an intervention may be superimposed on the three-dimensional image of the body volume being displayed to the physician.

Thus, from the X-ray system, the position of the swing arm is known at which the fluoroscopy data is generated and, therefore, a rendering of the three-dimensional volume data can be reconstructed using the same position of the swing arm as a reference. The two -dimensional fluoroscopy data and the three-dimensional rendering can then be displayed together.

Registration of the three-dimensional data with the two-dimensional fluoroscopy data is relatively straightforward (from the position of the swing arm) because the same X-ray system is used, with the same calibrated geometry, to generate both the two- and three -dimensional data.

However, it is not so straightforward if the three-dimensional image data has been acquired (prior to an intervention) using a different modality, such as CT (computerised tomography) or MR (magnetic resonance). There are a number of therapies in which the 'fusion' of pre-interventionally processed CT and/or MR image data with fluoroscopic image data acquired during an intervention may generate benefits. Examples of therapies suited to improvement by registration of fluoroscopic with MR images include those that involve access to soft tissue targets, such as tumours, by their relationship of the soft tissue to bony structures with confidence, and the fluoroscopy can give accurate information about the state of the bony structures (and, by inference, the soft tissue) during an interventional procedure. Therapies that could be improved by registration of fluoroscopic with CT images include those that involve access to structures which can be visualised by X-ray with the addition of contrast agents, but whose geometries are ambiguous in radiographically-projected images.

Thus, it is an object of the present invention top provide an image processing method and system which enables live two-dimensional image data captured in respect of a body volume, using a first imaging system, to be displayed relative to three-dimensional volume data captured using a second imaging system.

In accordance with the present invention, there is provided a system for displaying image data acquired during an intervention procedure in respect of a body volume, said system comprising means for receiving three-dimensional image data of said body volume acquired using a first imaging system, means for receiving two-dimensional image data in respect of said body volume acquired using said first imaging system during an intervention procedure, means for mapping said two-dimensional image data onto a corresponding region of said three-dimensional image data acquired using said first imaging system, means for receiving three-dimensional image data of said body volume acquired using a second imaging system of a different modality to said first imaging system, means for registering said three-dimensional image data acquired using said second imaging system with said three-dimensional data acquired using said first imaging system and thereby mapping said two-dimensional image data onto a corresponding region of said three-dimensional image data acquired using said second imaging system, and means for displaying said two-dimensional image data within said corresponding region of said three -dimensional image data of said body volume acquired using said second imaging system.

Also in accordance with the present invention there is provided a method for displaying image data acquired during an intervention procedure in respect of a body volume, the method comprising receiving three-dimensional image data of said body volume acquired using a first imaging system, receiving two-dimensional image data in respect of said body volume acquired using said first imaging system during an intervention procedure, mapping said two-dimensional image data onto a corresponding region of said three-dimensional image data acquired using said first imaging system, receiving three-dimensional image data of said body volume acquired using a second imaging system of a different modality to said first imaging system, registering said three-dimensional image data acquired using said second imaging system with said three-dimensional data acquired using said first imaging system and thereby mapping said two-dimensional image data onto a corresponding region of said three-dimensional image data acquired using said second imaging system, and displaying said two-dimensional image data within said corresponding region of said three -dimensional image data of said body volume acquired using said second imaging system.

The three-dimensional image data acquired using the first and/or second imaging systems is preferably acquired prior to the interventional procedure, and the two -dimensional image data is beneficially live and displayed substantially in real time within said corresponding region of said three-dimensional image data of said body volume acquired using said second imaging system.

The three-dimensional image data acquired by the first imaging means is beneficially acquired by means of a 3D rotational scan (preferably wherein a contrast agent is injected into the body volume), particularly since such a scan (e.g. 3 DRA) is routinely obtained prior to any intervention for diagnostic and treatment evaluation purposes. The two -dimensional image data may, for example, be acquired by means of X-ray fluoroscopic imaging means.

The three-dimensional image data acquired by the second imaging means may be acquired by means of a computerised tomography or magnetic resonance imaging system.

Preferably, live two-dimensional image data is superimposed on the three-dimensional image data only where two-dimensional image data is present. This may be achieved using blending means, wherein the two-dimensional pixel density is used as a blending factor.

These and other aspects of the present invention will be apparent from, and elucidated with reference to, the embodiments described herein.

Embodiments of the present invention will now be described by way of examples only and with reference to the accompanying drawings, in which.

Figure 1:
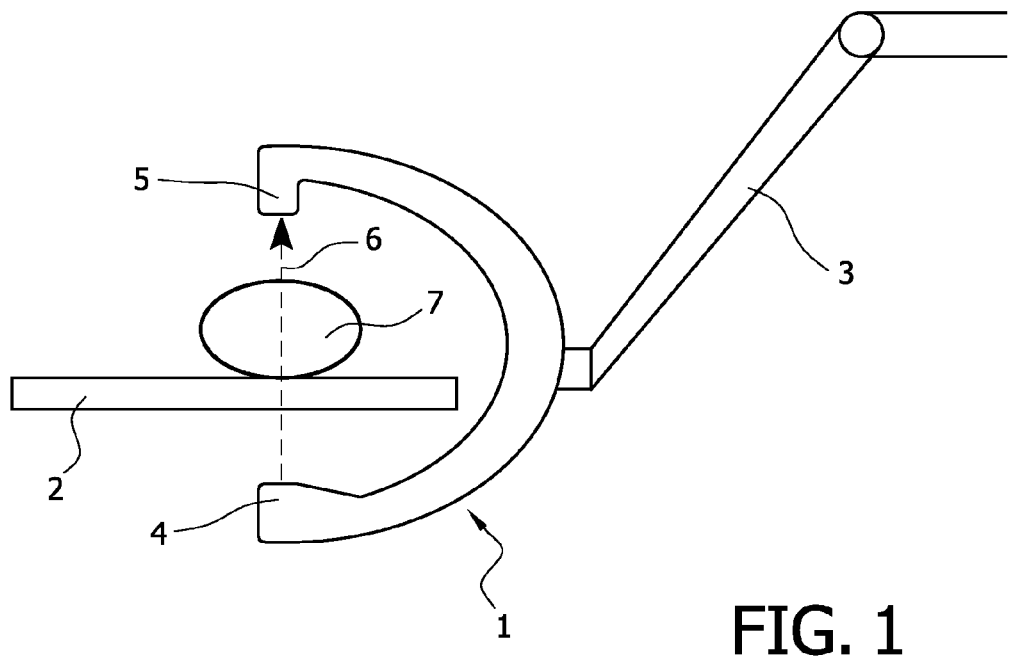
FIG. 1 is a schematic side view of an X-ray swing arm.
Figure 2:
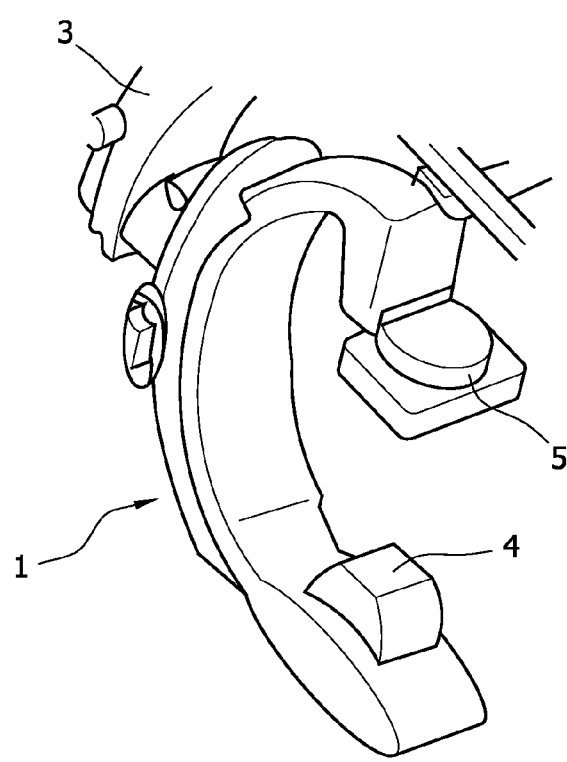
FIG. 2 is a perspective view of an X-ray swing arm.
Figure 3:
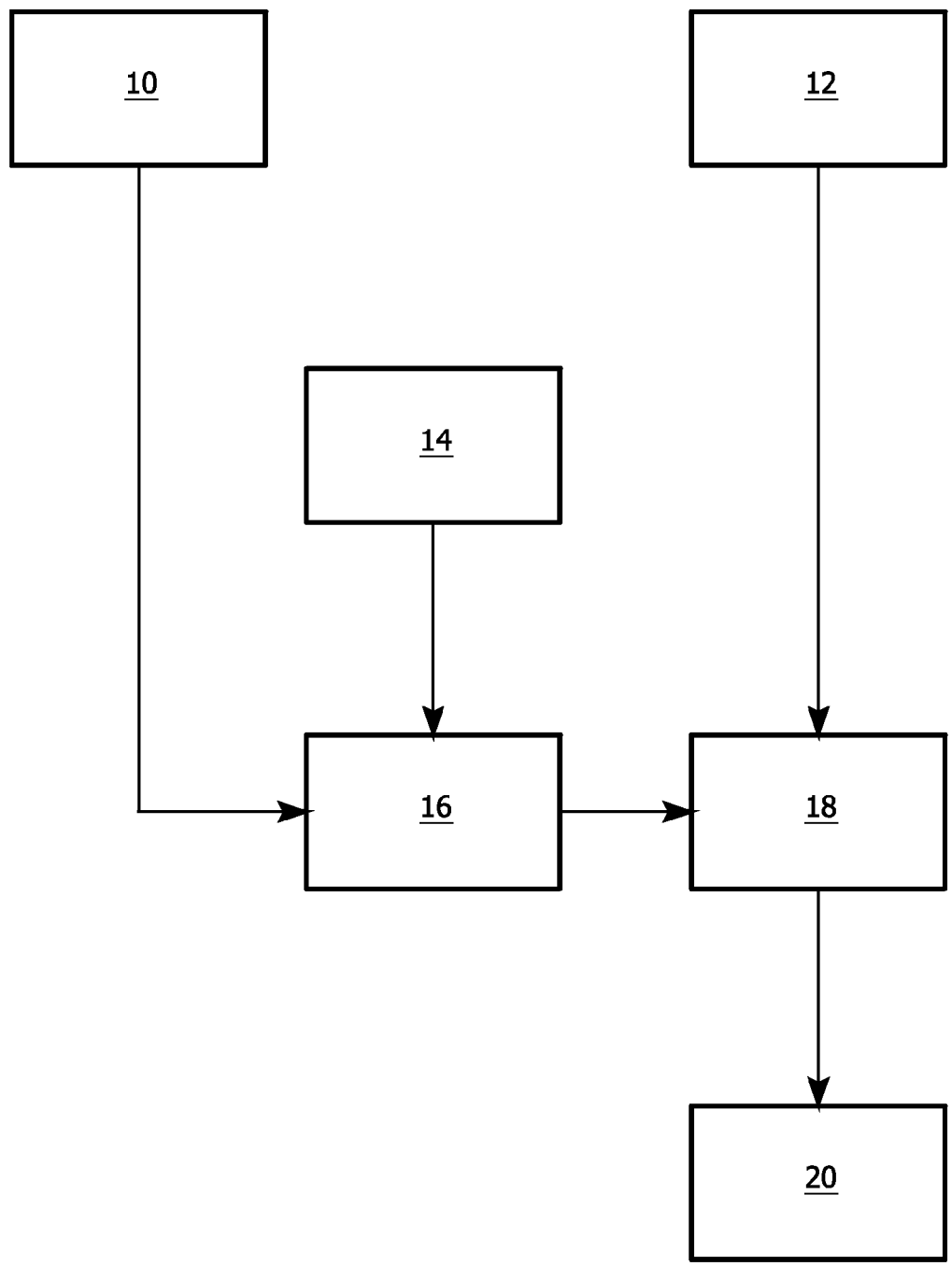
FIG. 3 is a schematic block diagram illustrating the principal components of an image processing system according to an exemplary embodiment of the present invention.

Referring to FIG. 3 of the drawings, prior to the intervention, a 3D rotational scan is acquired (at block 10) in respect of a body volume and reconstructed. In addition, three-dimensional image data in respect of the body volume is acquired (at block 12) using another modality, such as computerised tomography (CT) or magnetic resonance (MR), reconstructed, and prepared for visualisation. During the actual intervention, live two -dimensional fluoroscopic images are acquired (at block 14), using the same imaging system as that employed to acquire the above mentioned 3D rotational scan and processed for visualisation.

As stated above, there are many applications envisaged whereby it would be advantageous to enable registration of two-dimensional fluoroscopic image data and three -dimensional, e.g. CT or MR, image data. 2D-3D registration techniques have been proposed in the past. For example, L. Zollei et al, "2D-3D Registration of X-Ray Fluoroscopy and CT Images Using Mutual Information and Sparsely Sampled Histogram Estimators", IEEE 2001 describes a method for registering biplanar 2D fluoroscopic images to a 3D CT volume, which employs a known technique of alignment by maximization of mutual information. A mutual information-based registration algorithm is proposed which is intended to establish the proper alignment between the two types of image data via a stochastic gradient ascent strategy. The proposed method involves estimating probability density measures of image intensities with a sparse histogramming method which speeds up the derivation of gradient estimates required by the maximization procedure. Other proposals have investigated a number of similarity measures which are judged empirically by probing the space of transformations between the coordinate frames of a 3D volume and a biplanar 2D image, so as to enable a "ground truth" of the registration to be determined.

However, such known 2D-3D processes are still relatively complex, the present invention proposes a simplified 2D-3D process, whereby the 2D fluoroscopic image data is first registered to 3D image data acquired using the same modality as that used to acquire the 2D fluoroscopic image data. Thus, the 2D image data is first registered (at block 16) to the 3D rotational image data acquired and reconstructed in respect of the body volume of interest using a technique such as that described in U.S. Pat. No. 6,666,579.

In general, the incoming live 2D information must be positioned into the 3D -viewing pyramid and carefully lined up with the 3D-volume information. In order to position the 2D data in 3D-space, the geometry information as used during the 2D acquisition is used to establish a matching virtual camera set-up, viewing pyramid and line of side, which can be used for 3D visualisation.

Next, a 3D-3D registration process is employed (at block 18) to register the 3D image data acquired in respect of the same body volume using, for example, CT or MR imaging systems to the 3D rotational image data. One technique which may be suitable for this is described in U.S. Pat. No. 6,728,424 in which is calculated a statistical measure of likelihood for two volumetric images. The likelihood is calculated based on an assumption that the voxel values in two images in registration are probabilistically related. The likelihood is calculated for a plurality of relative transformations in iterative fashion until a transformation that maximises the likelihood is found. The transformation that maximises the likelihood provides an optimal registration and the parameters for the revised transform are output to the memory of a display module 20 in aligning the 2D fluoroscopic image and the 3D MR/CT image as a fused or composite image. However, other suitable 3D-3D registration techniques, such as matched point, will be known to a person skilled in the art.

The present invention is considered suitable for many applications, including cardiovascular X-ray systems.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for displaying image data acquired during an intervention procedure in respect of a body volume, said system comprising means (10) for receiving three-dimensional image data of said body volume acquired using a first imaging system, means (14) for receiving two-dimensional image data in respect of said body volume acquired using said first imaging system during an intervention procedure, means (16) for mapping said two-dimensional image data onto a corresponding region of said three-dimensional image data acquired using said first imaging system, means (12) for receiving three-dimensional image data of said body volume acquired using a second imaging system of a different modality to said first imaging system, means (18) for registering said three-dimensional image data acquired using said second imaging system with said three-dimensional data acquired using said first imaging system and thereby mapping said two-dimensional image data onto a corresponding region of said three-dimensional image data acquired using said second imaging system, and means (20) for displaying said two-dimensional image data within said corresponding region of said three-dimensional image data of said body volume acquired using said second imaging system.

2. A system according to claim 1, wherein the three-dimensional image data acquired using the first and/or second imaging systems is acquired prior to the interventional procedure.

3. A system according to claim 1, wherein the two-dimensional image data is live and displayed substantially in real time within said corresponding region of said three-dimensional image data of said body volume acquired using said second imaging system.

4. A system according to claim 1, wherein said three-dimensional image data acquired by the first imaging means is acquired by means of a 3D rotational scan.

5. A system according to claim 1, wherein said two-dimensional image data is acquired by means of X-ray fluoroscopic imaging means.

6. A system according to claim 1, wherein the three-dimensional image data acquired by the second imaging means is acquired by means of a computerised tomography or magnetic resonance imaging system.

7. A system according to claim 1, wherein live two-dimensional image data is superimposed on the three-dimensional image data only where two-dimensional image data is present.

8. A system according to claim 7, comprising blending means, wherein two-dimensional pixel density is used as a blending factor.

9. A method for displaying image data acquired during an intervention procedure in respect of a body volume, the method comprising receiving three-dimensional image data of said body volume acquired using a first imaging system, receiving two-dimensional image data in respect of said body volume acquired using said first imaging system during an intervention procedure, mapping said two-dimensional image data onto a corresponding region of said three-dimensional image data acquired using said first imaging system, receiving three-dimensional image data of said body volume acquired using a second imaging system of a different modality to said first imaging system, registering said three-dimensional image data acquired using said second imaging system with said three-dimensional data acquired using said first imaging system and thereby mapping said two-dimensional image data onto a corresponding region of said three-dimensional image data acquired using said second imaging system, and displaying said two-dimensional image data within said corresponding region of said three-dimensional image data of said body volume acquired using said second imaging system.

* * * * *